(12) United States Patent
Tang et al.

(10) Patent No.: US 8,133,423 B2
(45) Date of Patent: Mar. 13, 2012

(54) METHOD FOR FABRICATION OF SILICONE COMPOSITE WITH ANTIMICROBIAL COATING

(75) Inventors: Chak Yin Tang, Hong Kong (HK); Da-zhu Chen, Shenzhen (CN); Tai Man Yue, Hong Kong (HK); Yuen Yee Chan, Hong Kong (HK)

(73) Assignees: The Hong Kong Polytechnic University, Hong Kong (HK); The Chinese University of Hong Kong, Hong Kong (HK)

( * ) Notice: Subject to any disclaimer, the term of this patent is extended or adjusted under 35 U.S.C. 154(b) by 60 days.

(21) Appl. No.: 12/581,889

(22) Filed: Oct. 20, 2009

(65) Prior Publication Data

US 2011/0091669 A1    Apr. 21, 2011

(51) Int. Cl.
B29D 22/00 (2006.01)
B32B 9/04 (2006.01)
A61L 2/232 (2006.01)
B05D 1/36 (2006.01)
B28B 5/00 (2006.01)

(52) U.S. Cl. ....... 264/240; 428/446; 428/448; 428/34.1; 422/30; 427/258; 427/344; 264/241

(58) Field of Classification Search ............... 28/34.1, 28/35.7, 36.1, 36.2, 36.9, 36.91, 36.92, 68; 427/2.1–2.31; 264/632, 636, 637, 641, 650, 264/651

See application file for complete search history.

(56) References Cited

U.S. PATENT DOCUMENTS

| | | | |
|---|---|---|---|
| 3,620,873 A * | 11/1971 | Ehrreich et al. | 156/250 |
| 5,019,096 A * | 5/1991 | Fox et al. | 600/36 |
| 5,466,726 A | 11/1995 | Inoue et al. | |
| 5,567,495 A * | 10/1996 | Modak et al. | 428/36.9 |
| 5,820,607 A * | 10/1998 | Tcholakian et al. | 604/265 |
| 6,013,275 A * | 1/2000 | Konagaya et al. | 424/443 |
| 2002/0032434 A1 * | 3/2002 | Chudzik et al. | 604/890.1 |
| 2007/0123853 A1 * | 5/2007 | Nesbitt | 606/45 |

FOREIGN PATENT DOCUMENTS

| | | | |
|---|---|---|---|
| JP | 2000088153 A | * | 3/2000 |
| JP | 2000302687 A | * | 10/2000 |
| JP | 2000-88153 | | 3/2008 |

OTHER PUBLICATIONS

Ohko et al. Self Sterilizing and Self Cleaning of Silicone Catheters Coated with TiO2 Photocatalyst Thin Films. J. Biomedical Materials research Applied Biomaterials vol. 58, pp. 97-101 (2001).*

Masahiro Okada, Shoji Yasuda, Tsuyoshi Kimura, Mitsunobu Iwasaki Seishiro Ito, Akio Kishida, Tsutomu Furuzono, Optimization of amino group density on surfaces of titanium dioxide nanoparticles covalently bonded to a silicone substrate for antibacterial and cell adhesion activities, J. Biomed. Mater Res., vol. 76A, pp. 95-101 (2006).

Yoshihisa Ohko, Yosuke Utsumi, Chisa Niwa, Tetsu Tatsuma, Koichi Kobayakawa, Yuichi Satoh, Yoshinobu Kubota, Akira Fujishima, Self-Sterilizing and Self-Cleaning of Silicone Catheters Coated with TiO2 Photocatalyst Thin Films: A Preclinical Work, J. Biomed. Mater. Res., Appl. Biomater., vol. 58, pp. 97-101 (2001).

* cited by examiner

*Primary Examiner* — Timothy Meeks
*Assistant Examiner* — Francisco Tschen
(74) *Attorney, Agent, or Firm* — The Hong Kong Polytechnic University

(57) ABSTRACT

A method of fabricating silicone composite with a layer of antimicrobial coating, the method includes forming an antimicrobial mixture by adding a calculated amount of antimicrobial agent to a solution of water and alcohol, depositing the antimicrobial mixture in a container with a thickness of 0.1 μm to 10 μm, evaporating the water and alcohol of the antimicrobial mixture to form the layer of antimicrobial coating, adding silicone resin on top of the layer of antimicrobial coating and allow the silicone resin to permeate and crosslink with the layer of antimicrobial coating and removing the silicone composite with the layer of antimicrobial coating from the container.

4 Claims, 3 Drawing Sheets

METHOD FOR FABRICATION OF SILICONE COMPOSITE WITH ANTIMICROBIAL COATING

BACKGROUND OF THE INVENTION

1. Field of the Invention

The present invention relates to an antimicrobial article, more particularly, relates to fabrication of silicone composite with antimicrobial coating.

2. Description of the Related Art

Catheters and medical tubes are widely used to inject fluid and nutrients into arteries and veins, and to drain fluid or urine from urethra or internal organs. Nevertheless, catheter-associated infections are common, accounting for a large number of all nosocomial infections. Thus far, several types of catheters with antimicrobial effects have been developed, such as the silver-impregnated type, the $TiO_2$-coated type, and the aminoglycoside type. Among metals with antimicrobial properties, silver has raised interest of many researchers due to its excellent antimicrobial properties and low toxicity.

The key challenges with developing these types of catheters are how to incorporate antimicrobial agent or coating onto the substrate and how to improve its antimicrobial effectiveness. One conventional method of incorporating antimicrobial agent into the silicone substrate is by blending via solution casting or melt compounding. The antimicrobial effectiveness of the conventional methods are limited by the relatively low amount of antimicrobial particles on the composite surface. The majorities of the antimicrobial agents are bound up within the polymer matrix, and therefore, are not easy to release to the composite surface. The use of additional antimicrobial agents with these methods may not improve the antimicrobial property of the material.

In order to overcome the existing drawbacks, a method of fabricating a double layer of silicone rubber tube was proposed by providing an internal layer in which an antimicrobial agent of zeolite carrying metallic silver is added to a transparent silicone rubber as a matrix, and an external layer made of transparent silicone rubber and formed so as to cover the internal layer, as described in Japanese Pat. No. 2000-88153. This method reduced the amount of antimicrobial agent and the cost of the product. However, a drawback of this method is the poor interfacial adhesion between the internal layer and the external layer (cover layer).

In recent years, there is increasing interest in altering the surface properties of the silicone substrate (catheter) in order to improve the efficiency of sterilization. A thin layer of antimicrobial agent (e.g. $TiO_2$) coated onto the substrate surface by dipping the commercial catheter in an ethanol-water solution of a titanium dioxide sol and silicon oxide compounds, as described in J. Biomed. Mater. Res., Appl. Biomater., Vol. 58, pages 97-101 (2001), provides a good self-sterilizing and self-cleaning feature for the commercial catheter. An intermediate layer of modified silicone resin was taken to enhance the adhesion between $TiO_2$ antimicrobial layer and the silicone substrate. However, this method is limited to preparation of antimicrobial silicone products with a very thin coating layer (less than about 1 μm in thickness). Once the coating thickness is close to 2 μm, the poor adhesion between antimicrobial particles and the onset of microcracks are not acceptable.

More recently, a composite consisting of $TiO_2$ particle, the surface of which was modified with amino groups, and a silicone substrate through covalent bonding at their interface was developed, as described in J. Biomed. Mater. Res., Vol. 76A, pages 95-101 (2006). Although the obtained composite possesses good antimicrobial performance and strong bonding between $TiO_2$ and the silicone substrate, the wide application of this method is limited by the complicated operating procedures and the relatively low amount of antimicrobial powders conglutinated in the substrate surface. Thus, the antimicrobial effectiveness is not satisfying.

In view of the above shortcomings, there exists a need for a simple, cost-effective method of coating antimicrobial agent on a substrate with excellent adhesiveness and antimicrobial effectiveness.

SUMMARY OF THE INVENTION

According to an aspect of the present invention, a method of fabricating silicone composite with a layer of antimicrobial coating, the method includes forming an antimicrobial suspension by adding a calculated amount of antimicrobial agent to a solution of water and alcohol, depositing the antimicrobial mixture in a container with a thickness of 0.1 μm to 10 μm, evaporating the water and alcohol of the antimicrobial mixture to form the layer of antimicrobial coating, adding silicone resin on top of the layer of antimicrobial coating and allow the silicone resin to permeate and crosslink with the layer of antimicrobial coating and removing the silicone composite with the layer of antimicrobial coating from the container.

In accordance with another aspect of the present invention, an antimicrobial article prepared by a method includes forming an antimicrobial mixture by adding a calculated amount of antimicrobial agent to a solution of water and alcohol, depositing the antimicrobial mixture in a container with a thickness of 0.1 μm to 10 μm, evaporating the water and alcohol of the antimicrobial mixture to form the layer of antimicrobial coating, adding silicone resin on top of the layer of antimicrobial coating and allow the silicone resin to permeate and crosslink with the layer of antimicrobial coating, and removing the silicone composite with the layer of antimicrobial coating from the container.

Further features and aspects of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

The accompanying drawings, which are incorporated in and constitute a part of the specification, illustrate embodiments of the invention and, together with the description, serve to explain the principles of the invention.

The conventional methods to include antimicrobial agent in a silicone matrix may be performed using solution casting or melt compounding. The antimicrobial particles are dispersed within the matrix polymer. However, no inhomogeneity exists perpendicular to the composite surface. For this structure, the effective antimicrobial components are closely bounded by the polymer chains, which is not propitious to their release from the substrate. Thus, the antimicrobial effectiveness is significantly degraded.

The existing method typically involves surface-coating an antimicrobial layer on a pre-fabricated polymer substrate. The present invention takes an inverse approach to produce an antimicrobial coating layer onto the silicone substrate. More specifically, a thin layer of antimicrobial agent is initially prepared. Then, silicone resin is subsequently casted onto the layer of antimicrobial agent. After fully penetrating and curing, the antimicrobial coating layer containing silicone resin is formed on the surface of the silicone substrate.

FIGS. 1A to 1D illustrate the exemplary process sequence of the fabrication of silicone composite with antimicrobial coating according to an embodiment of the present invention. A solution of water and alcohol is first formed. The ratio of water to alcohol is approximately 1 to 3 by weight. In this example, 5 g of water and 15 g of alcohol is added to a container to form a solution. Then, a non-toxic and biocompatible antimicrobial agent is added to the solution. For instance, sodium zirconium phosphate that contains silver ion may be utilized as the antimicrobial agent. Other inorganic powders such as zinc oxide (ZnO), titanium dioxide ($TiO_2$), or zeolite containing silver ion may also be used.

The concentration of the antimicrobial agent is controlled as 0.11%, 0.57%, 1.14%, 2.28%, by weight for the calculated coating thickness of 0.1 µm, 0.5 µm, 1.0 µm, 2.0 µm, respectively, assuming that the deposition is dense. The layer of antimicrobial agent may be approximately 0.1 to 10 µm thick. Then, the resulting mixture is thoroughly stirred at room temperature, and follow by twenty minutes of ultrasonification at 25 kHz, 200 W.

Figure 1A:
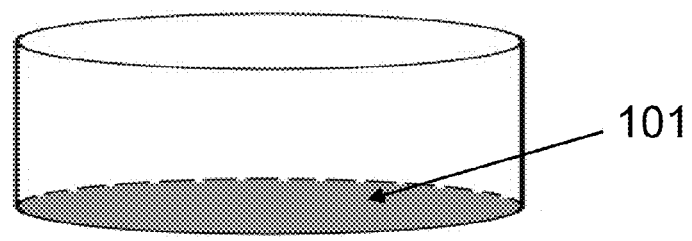
FIGS. 1A-1D illustrate an exemplary coating method according to an embodiment of the present invention.

Thereafter, the mixture is casted on a container such as a petri dish for evaporation. In order to speed up the evaporation of the solvent (i.e., water and alcohol), the mixture may be heated to 60° C. by a heating device. As a result, a thin layer of antimicrobial agent 101 of the calculated thickness is deposited on the bottom of Petri dish as shown in FIG. 1A.

Figure 1B:
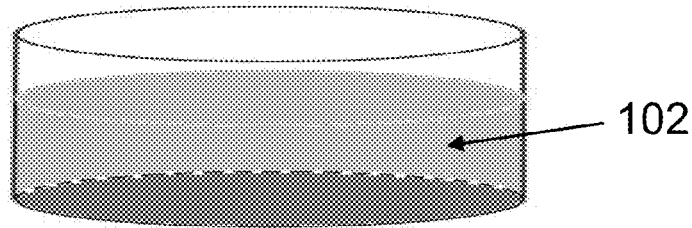

Next, a chloroform solution of silicone resin 102 is cast into the Petri dish containing antimicrobial layer as shown in FIG. 1B. The silicone resin may be an RTV silicone rubber such as Elastosil M 4600 US A/B made by RubberWorks Inc. It's a pourable, addition-curing high strength silicone that can be vulcanized at room temperature, or at elevated temperatures to increase the rate of cure. Silicone rubber Elastosil M 4600 US A/B contains components A and B. The transparent component A has a viscosity at 23° C. of 20,000 mPa and colorless component B has a viscosity at 23° C. of 12,000 mPa are used with a ratio of 10/1 by weight. The two silicone components are mixed and solved in chloroform.

Figure 1C:
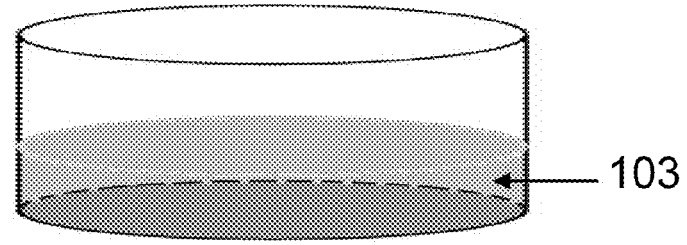

After the chloroform solution of silicone resin is casted onto the Petri dish that contains the antimicrobial layer, the silicone resin solution gradually permeated into the voids of antimicrobial particles due to the gravity. At the same time, as shown in FIG. 1C, the silicone resin 103 began to crosslink with the antimicrobial agent (i.e., silver ion), accompanied by solvent evaporation. As a result of permeation and crosslinking reaction, a strong interfacial adhesion of the silicone resin and the antimicrobial agent is achieved. The thickness of the silicone substrate may be varied depending on its application. The antimicrobial particles are thus fixed on the surface layer by cross-linked silicone resin, which may serve to perform fast sterilization.

Figure 1D:
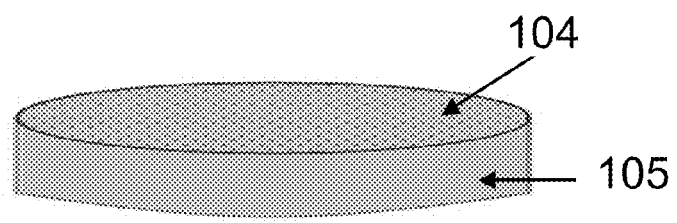
Figure 2:
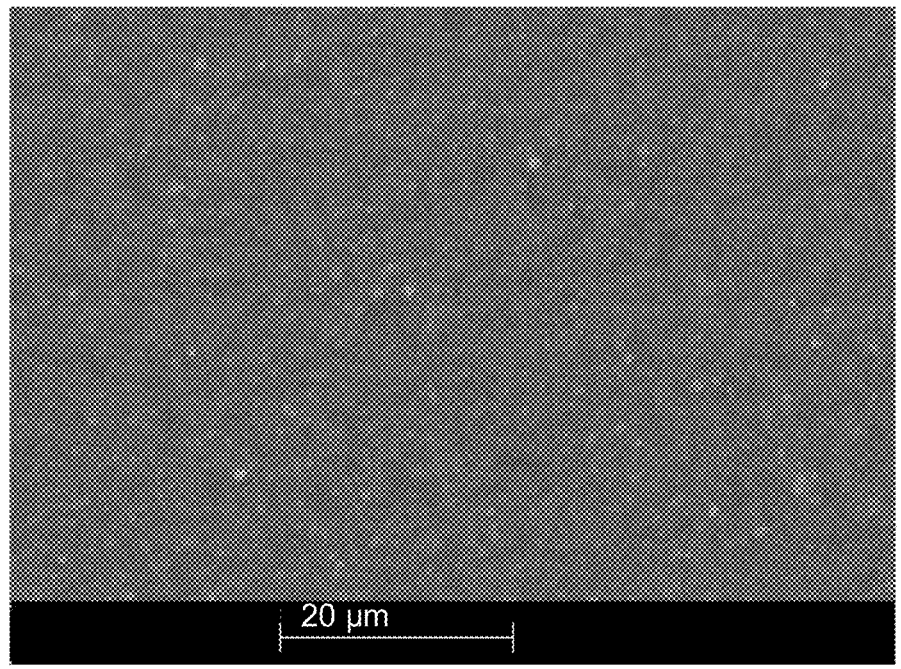
FIG. 2 is an SEM micrograph illustrating an observation of the surface of the antimicrobial coating layer.
Figure 3:
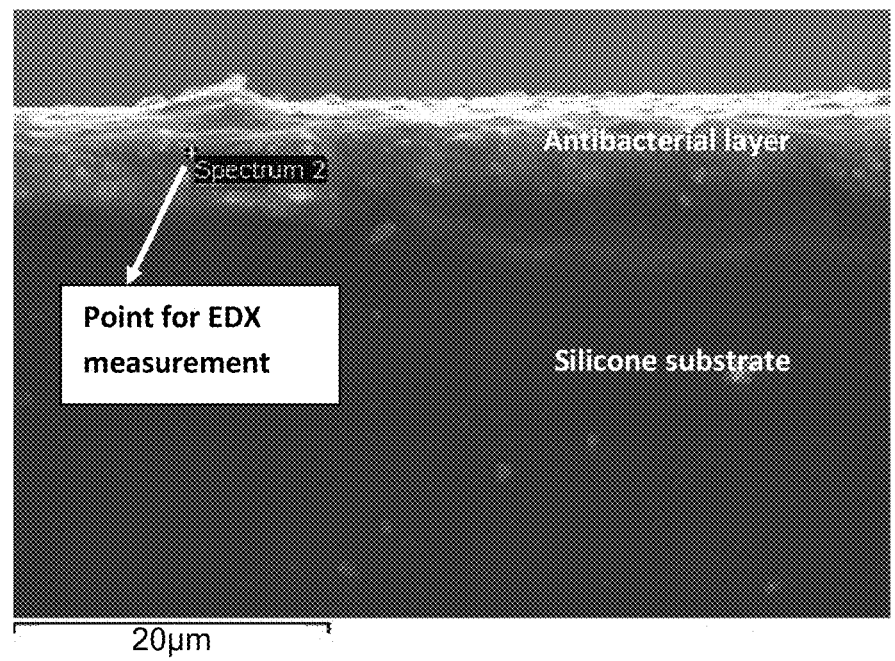
FIG. 3 is an SEM micrograph illustrating the cross-section of the antimicrobial layer.

Lastly, the silicone composite with an antimicrobial coating was obtained, which can be easily peeled off from the Petri dish as shown in FIG. 1D. The top layer 104 is an antimicrobial coating and the bottom layer 105 is a silicone composite. Many of the antimicrobial micro-particles were coated on the surface of the silicone resin matrix, which function as fast sterilization. The resulting coated silicone substrate may be cut into various shape and size. In lieu of using the petri dish, a special molding of various shape and size may be utilized. For instance, a tube shape molding may be used by using the above-described method to fabricate an antimicrobial coated medical catheter.

While the above example uses silver ion (Ag+) as the antimicrobial agent, other inorganic powder such as zinc oxide or titanium dioxide may also be used as the bioactive or antimicrobial agent.

Figure 4:
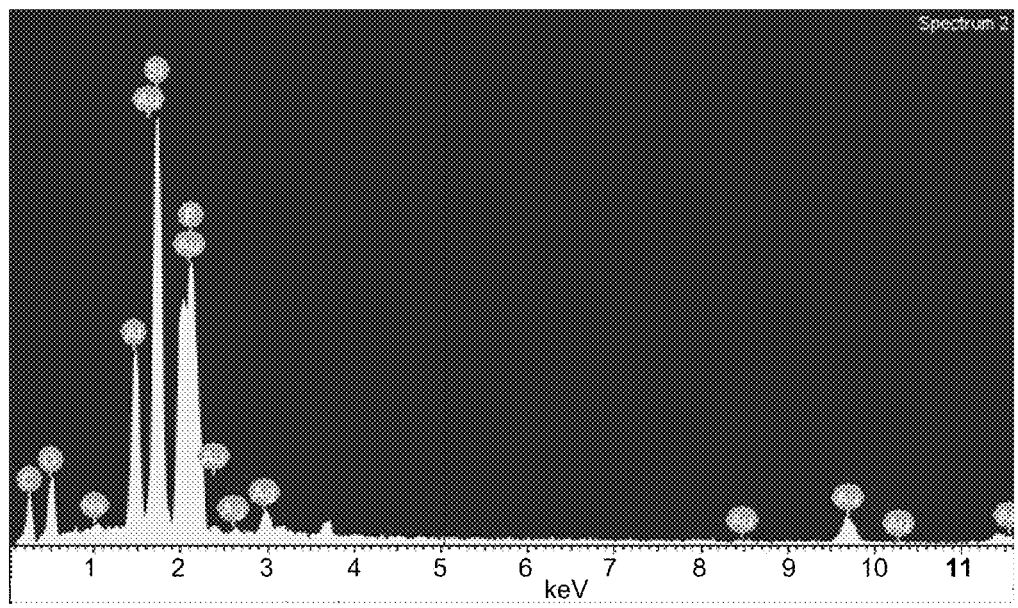
FIG. 4 is an EDX analysis of the antimicrobial coating.

The method has been used to prepare antimicrobial silicone composites with various thicknesses (0.1 to 2.0 µm). The scanning electron microscope (SEM) micrograph observation illustrates that inorganic particles are evenly distributed on the surface of the material. The cross-section observation also verifies the good adhesion between the substrate (silicone composites) and the antimicrobial coating. Also, FIG. 4 is an energy dispersive x-ray (EDX) analysis of the antimicrobial coating. It demonstrates that the presence of elements includes Ag, P and Si. Thus, there is not only effective antimicrobial component (silver ion) and its slow release carrier (phosphate), but also cross-linked silicone composites in the coating layer.

Figure 5:
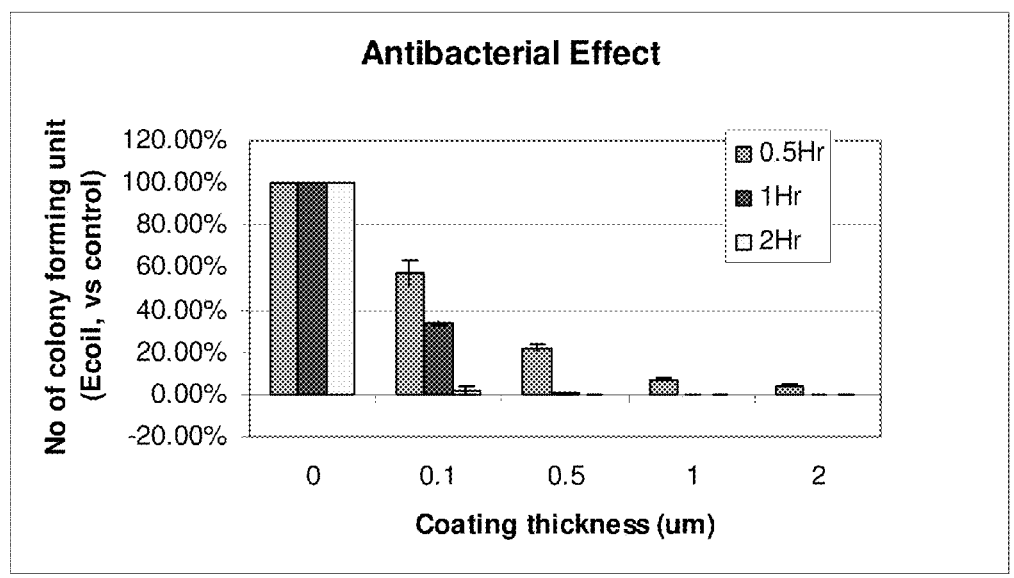
FIG. 5 illustrates the antimicrobial effectiveness of the antimicrobial coating.

FIG. 5 illustrates the antibacterial activity of the silicone composite. The antibacterial effectiveness is measured with different time duration from 30 minutes to 2 hours. As shown, with increasing thickness of antimicrobial coating (up to 2 µm) and time duration, the antibacterial effect is also increased.

In addition, cell viability on the antimicrobial article has also been measured. HL-60 (Human promyelocytic leukemia cells) has been incubated for 24 hours for various antimicrobial coating thicknesses (0.1 to 2.0 µm). The results indicate that the cell viability is over 98%.

As illustrated by the above-described experiments, the antimicrobial article contains excellent antimicrobial properties and low toxicity. In addition, by using the present method for fabricating an antimicrobial article, no amount of antimicrobial agent is wasted. As such, the present invention provides a simple, cost-effective method of coating antimicrobial agent on a substrate.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

What is claimed is:

1. A method of fabricating silicone composite with a layer of antimicrobial coating, the method comprising:
   forming an antimicrobial mixture by adding a calculated amount of antimicrobial agent to a solution of water and alcohol;
   depositing the antimicrobial mixture in a container, the antimicrobial mixture having a thickness of 0.1 µm to 10 µm;
   evaporating the water and alcohol of the antimicrobial mixture to form the layer of antimicrobial coating;

adding silicone resin on top of the layer of antimicrobial coating and allow the silicone resin to permeate and crosslink with the layer of antimicrobial coating; and removing the silicone composite with the layer of antimicrobial coating from the container.

2. The method according to claim 1, wherein the antimicrobial agent includes silver ion-containing sodium zirconium phosphate/zeolite, zinc oxide or titanium dioxide.

3. The method according to claim 1, wherein the silicone resin is room temperature vulcanizing (RTV) silicone rubber.

4. The method according to claim 1, wherein the solution of water and alcohol has a ratio of 1 to 3.

* * * * *